United States Patent [19]

Tsuda et al.

[11] 4,243,532
[45] Jan. 6, 1981

[54] BLOOD TREATING SYSTEM

[75] Inventors: Nobuaki Tsuda; Naoya Kominami; Kenji Inagaki; Tamotsu Imamiya, all of Fujishi, Japan

[73] Assignee: Asahi Kasei Kogyo Kabushiki Kaisha, Osaka, Japan

[21] Appl. No.: 968,914

[22] Filed: Dec. 13, 1978

Related U.S. Application Data

[63] Continuation of Ser. No. 726,193, Sep. 24, 1976, abandoned.

[30] Foreign Application Priority Data

Sep. 26, 1975 [JP] Japan .................................. 50-115662
Mar. 29, 1976 [JP] Japan .................................. 51-33562

[51] Int. Cl.³ ............................................ B01D 31/00
[52] U.S. Cl. .................................. 210/196; 210/321.1; 210/434; 210/927
[58] Field of Search ............... 210/23 F, 27, 434, 196, 210/321 B, 321 A, 321 R, DIG. 23, 502; 128/214 R

[56] References Cited

U.S. PATENT DOCUMENTS

| | | | |
|---|---|---|---|
| 3,888,250 | 6/1975 | Hill | 210/502 X |
| 4,013,564 | 3/1977 | Nose | 210/321 B |

*Primary Examiner*—Frank A. Spear, Jr.
*Attorney, Agent, or Firm*—Armstrong, Nikaido, Marmelstein & Kubovcik

[57] ABSTRACT

A blood-treating system in which apparatus for the purification of blood by purifying blood plasma, is provided. The system includes as principal elements, an apparatus for separating blood plasma by way of a membrane, an apparatus for purifying blood plasma and an apparatus for mixing blood with blood plasma to be placed between a blood-introducing portion and a purified blood-withdrawing portion of the system. This system can remove useless substances from blood with a high efficiency without damaging and reducing blood cell components or any fear of mixing of the fine powder in the purifying agent.

7 Claims, 6 Drawing Figures

BLOOD TREATING SYSTEM

This is a continuation of application Ser. No. 726,193, filed Sept. 24, 1976, now abandoned.

DESCRIPTION OF THE INVENTION

The present invention relates to an effective blood-treating system for purifying blood by removing useless substances contained therein.

It has recently been found that certain types of substances are accumulated in the blood in some diseases such as renal insufficiency, hepatic insufficiency, etc., and this has been a probelm awaiting solution.

In the case of renal insufficiency, urea, creatinine, uric acid, etc. and a group of substances referred to as uremic toxin and having not yet been sufficiently elucidated, occur in the blood and in the case of hepatic insufficiency, ammonia, fatty acids, amines and many groups of other substances occur have come into question.

Further, if a medicine such as a sleeping drug or a poison is put into the body large amounts and a poison condition is brought about, it is said that the medicine or poison is existent in a high concentration in blood.

In order to improve the body condition by removing the above-mentioned substances (useless substances), various ideas have been proposed and studies have been made. For example, there have been proposed ideas involving purifying blood by treating it according to a dialysis-ultrafiltration method utilizing a membrane in order to remove useless substances, as in the case of an artificial kidney.

On the other hand, there has been also proposed a method wherein blood is treated by contacting it directly with an adsorbent (purifying agent) such as active carbon, etc. to remove useless substances by adsorption. This method, however, has a big defect because blood cell components are damaged by a purifying agent such as active carbon, etc. Namely, characteristic features of blood are injured on account of destruction of erythrocyte (hemolysis) or a remarkable reduction in platelets. Further, emboli are formed inside the capillary vascula of a living body by fine powder from a purifying agent such as active carbon, etc. flowing into blood. In order to solve these problems, improvements have been made along the following two directions. One direction is to select a purifying agent which does not form fine powder. Resins such as ion-exchange resins, etc. have been employed therefor. The other is to encapsulate a purifying agent such as active carbon into a so-called microcapsule.

Although the above-mentioned matters have been partially improved, such improvements are insufficient. Namely, "resins" are still quite questionable since they cause a considerable damage and reduction of blood cell components. Also, active carbon encapsulated into microcapsules causes considerable damage and reduction of blood cell components and the flowing-out of fine powder. In addition, such active carbon is further questionable because the capacity of removal by adsorption is reduced by encapsulation into microcapsules.

The present inventors have been studying for many years in order to solve the above-mentioned various problems revealed in the prior art relative to blood-purifying treatments, namely in order to develop a blood-treating apparatus which can remove useless substances with a high efficiency without damaging and reducing blood cell components and with much less fear of the fine powder of a purifying agent flowing into blood; which is safe in all of the circulation systems outside a living body, from taking out blood from a body and subjecting it to purifying treatment to returning it to the body; and further which is simple in handling.

In these studies, the present inventors paid attention to the fact which has recently been clarified in the art, i.e., "almost all of the useless substances in blood are existent in blood plasma", and thus got an idea for purifying blood by removing useless substances from this plasma. After carrying out numbers of experiments, the present inventors have completed the method of the present invention.

The present invention resides in:

a blood-treating system which comprises, as the main elements, a plasma-separating apparatus for separating plasma by means of a membrane, a plasma-purifying apparatus for removing useless substances contained in the separated plasma and an apparatus for mixing blood with the resulting plasma, all located between a blood-introducing portion and a purified blood-withdrawing portion.

The blood-introducing portion referred to herein is an apparatus for taking outblood by means of a shunt or the like and introducing the blood into the main elements of the blood-treating system, and is constructed from members selected optionally according to necessity from among a leading pipe, a cock, an inlet through which heparin is introduced, a bubble trap, a sampling tube, a pump and others of a similar nature.

The purified blood-withdrawing portion referred to herein is an apparatus for withdrawing the blood purified by the main elements of the blood-treating system, by means of a shunt or the like, and is constructed from members selected optionally according to necessity from among a leading pipe, a cock, a sampling tube, a bubble trap and others of a similar nature.

The present invention will be further illustrated by the accompanying drawings.

Figure 1:
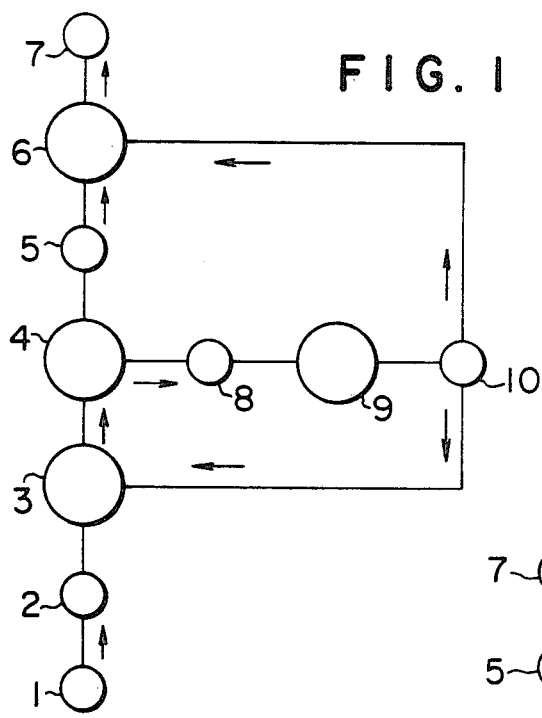
FIGS. 1–3 are flow sheets which illustrate the construction of the apparatus of the present invention.

In FIG. 1, a basic flow of the blood-treating system of the present invention is shown.

The system of the present invention will be explained below in accordance with the flow of blood.

Blood is introduced from a blood inlet 1 of the blood-introducing portion and sent to a blood-separating apparatus 4 via an apparatus for mixing blood with plasma 3, if necessary, by means of a pump 2. Plasma is separated at a plasma-separating apparatus 4. Remaining blood reaches a purified blood-withdrawing port 7, via a blood pressure-regulator 5 and an apparatus for mixing blood with plasma 6.

The plasma separated at the plasma-separating apparatus 4 is sent by means of a pump 8 to a plasma-purifying apparatus 9, where useless substances contained in the plasma are removed by adsorption. Further, the fine powder of a purifying agent which becomes a cause of emboli inside the capillary vascula of a living body is separated. The resulting purified plasma is sent to apparatus 3 or 6 selected in a predetermined manner by a three-way-cock 10, for mixing blood with plasma, where plasma is mixed with blood.

When the plasma purified in the plasma-purifying apparatus 9 is led to the apparatus for mixing blood with plasma 3, the purified plasma is mixed with blood introduced from the blood-introducing portion and again enters the plasma-separating apparatus 4. Namely, while useless substances are removed (for purification) from the plasma during the circulation and returning movement of the plasma through the blood-treating apparatus, a part of the plasma is always discharged from the purified blood-withdrawing port 7. If blood-treatment is carried out in this manner, the hematocrit value of the blood entering the plasma-separating means 4 can be reduced, whereby the damage to the blood cell components at the plasma-separating apparatus 4 can be reduced further and also a larger amount of plasma can be separated.

When purified plasma is led to the blood and blood plasma-mixing apparatus 6, it is mixed with the blood coming from the plasma-separating vessel 4 and led to the purified blood-withdrawing port 7. According to this process, since the concentration of useless substances in a separated plasma is high, the purification of plasma is carried out effectively in the plasma-purifying apparatus 9.

The selection of the path for channeling a purified plasma to the blood and blood-plasma-mixing apparatuses, is usually made at the time of clinical treatment. Namely, when the blood-circulation condition of a body is good and a sufficient amount of flow of blood can be led to the blood-introducing inlet 1, it is preferable to lead the purified plasma to the blood and blood plasma-mixing apparatus 6. In other cases, it is preferable to lead the plasma to the blood and blood plasma-mixing apparatus 3. It is possible to carry out the selection and change at an optional time, quickly, safely and with certainty, even at the time of clinical treatment by operating a three-way cock. The same effect can be achieved by stopping the leading pipe to the blood and blood plasma-mixing apparatus 3 or 6 with forceps or stoppers by using a Y-way tube in place of a three-way cock 10.

In the blood-treating system of the present invention, since there are blood and blood plasma-mixing apparatuses 3 and 6 before and after the plasma-separating apparatus 4 as shown in FIG. 1, purified plasma can be led to any of these two apparatuses easily, quickly, safely and with certainty. Thus, it enables the carrying out of purification treatments of blood clinically according to a method most suitable to the blood-circulation condition of patients. Thus, a great total treating effectiveness is exhibited. This is a feature of the system of the present invention.

Figure 2:
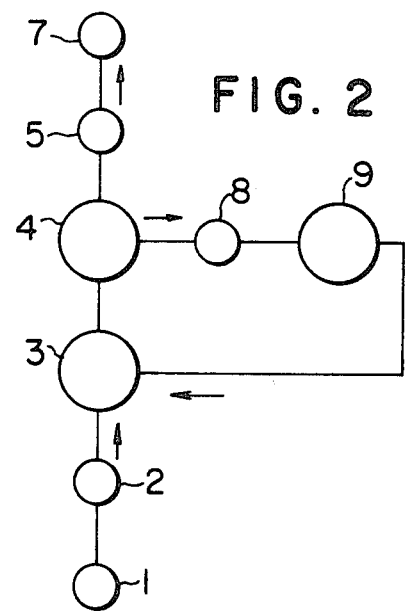
Figure 3:
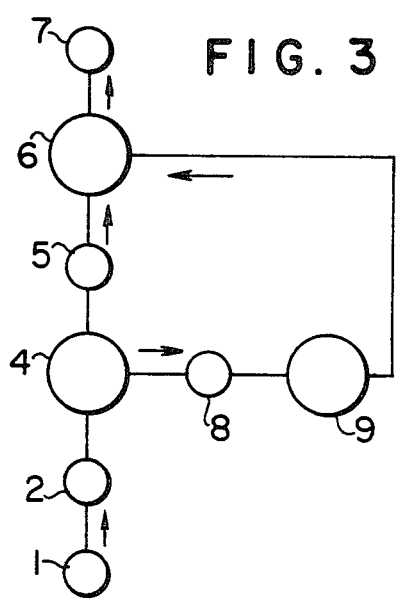

As is clear from the foregoing description, in the blood-treating system of the present invention, the object of blood purification can be achieved sufficiently even with basic flows shown in FIGS. 2 and 3 wherein a single blood and blood plasma-mixing apparatus is provided. FIG. 2 shows a case where only a blood and blood plasma-mixing apparatus 3 is provided. In this case, the blood introduced from a blood-introducing port 1 is sent, if necessary, by way of a pump 2, through a blood and blood plasma-mixing apparatus 3 to a plasma-separating apparatus 4 where the plasma is separated and led to a purified blood-withdrawing port 7. The plasma separated at the plasma-separating apparatus 4 is sent by a pump 8 to a plasma-purifying apparatus 9. After the purification of plasma, and filtration of the fine powder have been carried out, it is led to the blood and blood-plasma mixing apparatus 3 where it is mixed with the blood introduced from the blood-introducing port 1, and then led to the plasma-separating apparatus 4.

FIG. 3 shows a case where only a blood and blood plasma-mixing apparatus 6 are provided. In this case, the blood introduced from a blood-introducing port 1 is sent, if necessary, by way of a pump 2, to the plasma-separating apparatus 4 where plasma is separated, passes through the blood pressure regulator 5 and then enters the blood and blood plasma mixing apparatus 6 where it is mixed with the purified plasma, and the resulting mixture is withdrawn from a purified blood-withdrawing port 7.

Figure 4:
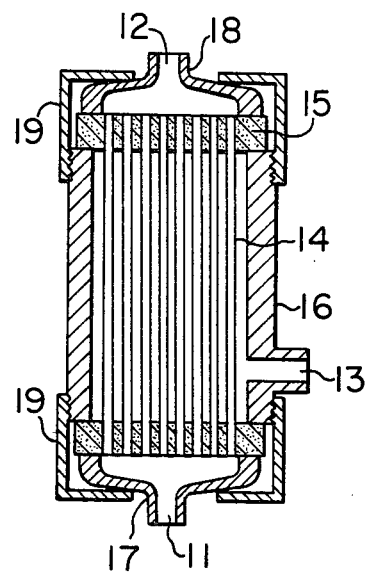
FIG. 4 is a schematic cross-sectional view of a plasma-separating apparatus in the system of the present invention.

As plasma-separating apparatuses, for example those having such a structure as shown in FIG. 4 are used.

FIG. 4 shows a cross-sectional view showing one example of plasma-separating apparatus.

The apparatus of FIG. 4 contains a blood inlet 11, a blood outlet 12, a plasma outlet 13 and a plurality of hollow fibers 14 filled on the inside. The ends of the hollow fibers form adhered and hardened parts with adhesive 15. In the vicinity of the hardened parts, nozzles 17 and 18 having the blood inlet 11 and blood outlet 12 which, are clamped with caps 19 and these are mated with the screw part of the main body 16. This structure is adapted for instances where blood is caused to flow through the hollow parts of the hollow fibers, and plasma migrates from the hollow parts of the hollow fibers to the outside. The plasma-separating apparatus having a structure in which blood is caused to flow outside the hollow fibers and plasma migrates into the hollow parts can also be used in the present invention.

The plasma-separating apparatus of FIG. 4 is one example in which the membranes of hollow fibers are used as plasma-separating apparatus. When flat membranes are used as plasma-separating apparatus, a structure which is the same as an artificial kidney dialyzer and generally called a "Kiil type" can be used as a plasma-separating apparatus, and when envelop-form membranes are used, a structure which is the same as the dialyzer and called a "coil type", can be used.

As plasma-separating membranes in the present invention, all kinds of membranes are useful so long as they can pass plasma, (whose important principal components are globulin, albumin, etc.), without passing blood cells. For that purpose, it is necessary that the pore size of membrane is less than $1\mu$ and greater than 80 A though this varies depending upon the shape of pore. In general, if the pore size becomes $1\mu$ or more, it is not preferable because a part of erythrocyte, platelet, etc. passes through the membranes and is mixed with separated plasma, resulting in hemolysis and reduction of blood cells. if the pore size is 80 A or less, protein in the blood cannot be separated sufficiently and so-called "plasma" cannot be obtained. It is said that a part of the useless substances which are accumulated in the blood (plasma) in various diseases, exists in a state where it is combined with the protein. Since sufficient separation of protein is necessary, a pore size of 80 A or less is not preferable. In general, the smaller the pore size, the slower the separation speed.

In view of the foregoing, it is preferable that the pore size of the membranes for use in plasma separation be in the range of $0.8\mu$–$0.05\mu$.

Since these membranes contact directly with blood, they must be safe, nontoxic and harmless. As membrane materials, cellulose acetate, polyacrylonitrile, nylon, polyester, polycarbonate, polyvinyl chloride, and other membrane materials useful in an artificial kidney can be used. Among these, a membrane which utilizes cellulose acetate, shows less tendency for clogging during the time of use, and maintains plasma-separation capacity for a longer time and hence is particularly preferable. The membranes can be used in the form of a flat membrane, envelope or hollow fibers. They are used by being assembled in a plasma-separating apparatus having a structure suitable for that purpose.

Among them, hollow fibers are preferable because many advantages have been found in the use of hollow fibers, such as higher plasma-separating efficiency, less reduction or less tendency of damage of blood cells, etc.

Heretofore, a centrifugal separator has been used for separating plasma. Recently, a centrifugal separator which can treat blood continuously to obtain plasma has been developed and used to some extent, but since the separation of plasma and blood cells is not sufficient, it is not preferable to use this separator as the plasma-separating apparatus of the present invention because it brings about reduction and damage to cells.

Figure 5:
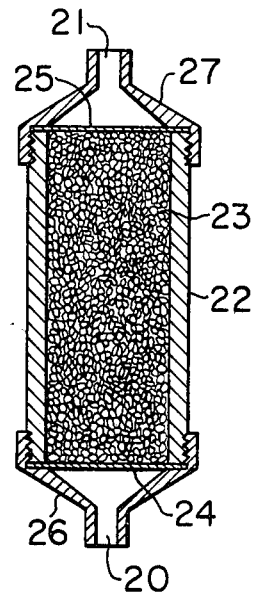
FIG. 5 is a schematic cross-sectional view of a plasma-purifying apparatus used in the system of the present invention.

As plasma-purifying apparatus 9, for example, an apparatus having a plasma inlet 20, a plasma outlet 21, and a treating agent 23 of useless substances contained inside the main body 22 is used as shown in FIG. 5. In this apparatus, filters 24 and 25 are clamped by the main body and the nozzles 26 and 27 are connectd in a threaded manner with the main body in order to prevent the treating agent for useless substances from flowing out. Thus, the filter performs the function of preventing the flowing out of the treating agent for plasma purification and passing the plasma alone. It is necessary on this account to select one which is suitable to the property of the treating agent for plasma purification.

For example when a fine powder form of treating agent for plasma purification is used, the filter must be one having a sufficiently small pore size in order not to allow the fine powder to flow out. Even when a treating agent for plasma purification having a relatively large particle size is used, if it has the property of being easily pulverized and caused to flow out, the filter must have a sufficiently small pore size in order not to allow fine powder to flow out. In general those having pore size in the range of $1000\mu$ to $0.05\mu$, preferably $200\mu$ to $0.1\mu$, and, further, a uniformity of particle size are preferable. It is preferable to use a filter having a pore size equal to or greater than that of the membrane of the plasma separator 4 because of the reduction of useless substances in plasma.

The filter may be constructed as a combination of a plurality of filters having different pore sizes. It is preferable to use a plurality of filters having different pore sizes which are overlaid on and intimately adhered to each other, since the filter strength is increased thereby. A method in which a plurality of filters having different pore sizes are placed apart from each other within the flow way of plasma is suitable to an instance where a treating agent for plasma purification which is of a comparatively large particle size and liable to be pulverized easily in use. Since a filter having a larger pore size at first prevents larger particles from flowing-out and another filter having a smaller pore size prevents fine powders from flowing-out, clogging of filter mesh becomes less frequent. In such a case, it is preferable to place the filter having a smaller pore size in the circuit of plasma outside the plasma purification apparatus 9, for example, between the plasma purification apparatus 9 and blood and blood plasma-mixing apparatus 3 or 6 because a larger filtration area can be easily taken. It may be possible to construct a filter with one large flat membrane, but also used are those referred to as the "Kiil type" which are made of overlaid flat membranes as in the case of artificial kidney dializer, those referred to as the "coil type" which are made by winding up membranes of envelope form and also those having the same structure as that of the plasma-separating apparatus 3 which utilizes hollow fibers. Particularly those which utilize hollow fibers are preferable because they provide larger filtration areas with smaller volumes.

As for properties of filters, any one is useful so long as it is safe to living bodies. For example, stainless steel, polystyrene, polypropylene, nylon, polyester, silicone, teflon, polycarbonate, cellulose acetate, polyacrylonitrile and others which are used in artificial kidneys, and the like. Any of these can be used alone or in a combination. Any style or form of these raw materials can be used. Namely net-form, cloth form, membrane form, foam form and other forms of these materials can be used.

In the conventional methods wherein blood is directly contacted with a treating agent for plasma purification, the removal of fine powder from the treating agent for plasma purification has not been sufficient because a filter having a pore size which allows the passage of erythrocyte and leucocyte, etc., which are large particles in the blood, must be used. In the method of the present invention, since the important substances in the plasma are very small particles and hence a filter having a sufficiently small pore size can be used, the prevention of flowing-out of fine powder can be sufficiently carried out.

In the plasma purification apparatus of the present invention, active carbon, alumina, silica, alumina-silica, zirconium phosphate, zeolite, ion-exchange resin, etc. can be used as a purifying agent.

Active carbon is particularly preferable because various kinds of useless substances can be removed by adsorption with relatively good efficiency.

These purifying agents can be used in alone or as a mixture of two or more kinds thereof. For example, a mixture of active carbon and zirconium sodium phosphate can remove organic useless substances and ammonia effectively. These purifying agents can be used in any form such as globular, powdered, pellet, fibrous forms or the like.

Since blood cells (such as erythrocyte, platelet, etc.) do not contact the purifying agent in the system of the present invention, there is no need for fear of damage and reduction of blood cells brought about by the purifying agent. This, the purifying agent can be used even without being encapsulated into microcapsules. However, it is also possible to use the agent in the form of microcapsules, or the like.

Since active carbon or the like can be used in its natural state as a purifying agent in the system of the present invention, useless substances in plasma can be removed by adsorption with an extremely high efficiency and plasma can be sufficiently purified. Further since the fine powder of purifying agent can be filtered out with a filter having a smaller pore size, it is possible to prepare purified plasma which does not contain the fine powder of a purifying agent which can be a cause of embolisms inside the capillary vascula of a living body.

Figure 6:
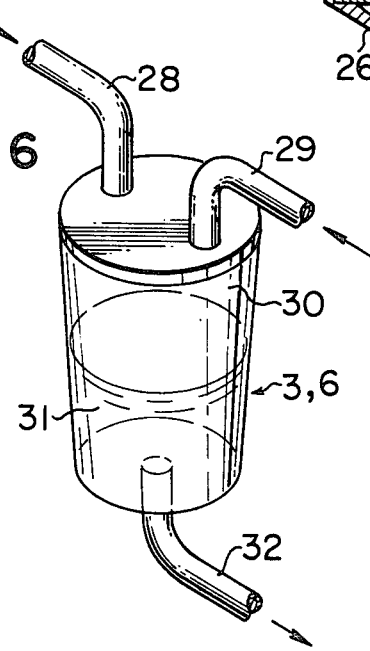
FIG. 6 is a perspective view of the apparatus for mixing blood with plasma.

The blood and blood plasma-mixing apparatus 3 or 6 of the present invention is an apparatus used to mix purified plasma and blood as above-mentioned, and its structure is as illustrated in FIG. 6. Blood is fed through an introducing pipe 28. Purified blood is fed through an introducing pipe 29 to form a mixed blood 31 which is sent to the next apparatus through a leading pipe 32. It is preferable to install an air-collecting space 30 at the upper part of the inside of the said mixing apparatus in order to draw out air.

The following non-limitative examples are provided to illustrate the apparatus of the present invention.

EXAMPLE 1

By using a plasma-separating apparatus, a plasma-purifying apparatus and a blood and blood plasma-mixing apparatus shown respectively in FIGS. 4, 5 and 6, a blood-treating system shown in the flow sheet of FIG. 3 was constructed.

As a plasma-separating membrane, cellulose acetate hollow fibers (having an outside diameter of 500$\mu$, an inside diameter of 300$\mu$, an effective length of 19 cm and a number of filaments of 2100 and a pore size of 0.2$\mu$) were used. As a plasma-purifying agent, 150 g of globular active carbon was used. As filters for plasma-purifying apparatus, a polypropylene mesh having a pore size of 5 mm and a polyester mesh having a pore size of 150$\mu$ were used by adhering these two in order to prevent the active carbon particles from flowing out. Further, an apparatus which is the same as the plasma-separator was provided between a plasma-purifying apparatus 9 and a blood and blood plasma-mixing apparatus 6 and use as a filter for filtering pulverized carbon.

By using this blood-treating system and a dog suffering from hepatic insufficiency, an experimentation in vivo was carried out.

A dog weighing 18 Kg was injected via vein with dimethylinitrosoamine (DMNA) at a dosage of 10 mg/Kg of body weight/day, for 3 days to create hepatic insufficiency.

An A-V shunt was formed between the femoral artery and vein. After heparinization of the whole body, circulation outside the body was carried out for 2 hours by way of the blood-treating system. The flow amount of blood introduced was 100-200 ml/min., plasma flux was 20-50 ml/min. and there was observed no reduction with lapse of time. The pressures before and after the plasma-separating apparatus were regulated with a blood pressure regulator so as to give a value of 180-100 mmHg.

As a result, movement of the body which had not been observed before treatment was observed notably. It is believed that the treatment with the system of the present invention is extremely effective. However, the dog died 2 days thereafter.

The result of anatomy revealed that the internal organs such as liver of the dog had been extremely regenerated compared with those of a control dog (DMNA was similarly injected for 3 days and died one day after three days of injections). There was observed no embolis which is considered to be caused by the fine powder of the carbon. The results of blood cell test before and after the treatment with the present system were as follows.

|  | before |  | after |
|---|---|---|---|
| erythrocyte | 480 $\times$ 10$^4$ | $\rightarrow$ | 479 $\times$ 10$^4$ |
| platelet | 18 $\times$ 10$^4$ | $\rightarrow$ | 18 $\times$ 10$^4$ |

There were no reductions in either. There was observed no hemolytic hemoglobin (<5 mg/dl) in the plasma separated with the plasma-separating apparatus.

EXAMPLES 2 to 4

Tests in vivo were carried out by using dogs loaded with drugs. The system and method used and the results are all indicated in Table 1. Namely, in the experiment of Example 2, a blood-treating system was constructed in accordance with the basic flow sheet shown in FIG. 2, by assembling a plasma-separating apparatus which uses polyacrylonitrile hollow fibers; a plasma-purifying apparatus which uses active carbon as a purifying agent and a polyester mesh as a filter; a cellulose acetate filter separately provided for filtering fine powder of carbon; a blood and blood plasma-mixing apparatus; and other means. A test was carried out by using a creatinine-loaded dog. As a result the creatinine concentration in blood after treatment was 25% of the value before the treatment. The reductions of erythrocyte and platelet were extremely small.

In the experiment of Example 3, a blood-treating system was assembled in accordance with the flow sheet of FIG. 1, but in the actual treatment a flow which is the same as that of FIG. 2 was used. In the plasma-separating apparatus, flat membranes of polycarbonate were overlaid, as in the "Kiil type" dializer of the artificial kidney and used. After the treatment, the movement of body of the dog was observed and after 7 hours, the dog stood up.

In the experiment of Example 4, an apparatus was assembled in accordance with the flow sheet of FIG. 1, but the treatment was carried out in accordance with a flow which is the same with that of FIG. 3. The dog stood up 3 hours after treatment.

The dogs used in the above-mentioned experiments were sacrificed and observed by anatomy, but there were no fine powders of the purifying agent and no embolisms which are considered to be caused by the fine powder of the purifying agent.

EXAMPLE 5

By using a system identical to that of Example 1 and in order to measure the amount of flow of fine powder of purifying agent, the system was operated while a sufficiently purified saline water was introduced from the blood inlet 1. The number of corpuscles of the saline water discharged from the purified blood outlet 7 was measured with a Coulter counter, but the increase in the number of corpuscles due to the passage through the present blood-treating system was few (number of increase of corpuscles of 2$\mu$-20 $\mu$ was 5/cc).

TABLE 1

| No. | Basic flow sheet | Plasma-separating apparatus, membrane, pore size and area | Plasma-purifying apparatus, purifying agent, filter material and pore size | Weight of dog (Kg) | Name of loaded drugs, loaded amount | Extra-corporeal circulation blood flow and time | Residual concentration ratio of drug in blood | Reduction of blood cells | Movement of body |
|---|---|---|---|---|---|---|---|---|---|
| 2 | Figure 2 | polyacrylonitrile hollow fiber, 0.1μ, 1 m² | active carbon 150 g, polyester 150 μ (outside the purifying apparatus), cellulose acetate, 0.3 μ | 20 | creatinine 50 mg/kg | 150 ml–200 ml/min 4 hr. | 25% | erythrocyte 3% platelet 2% | Yes from the starting |
| 3 | Figure 1 (Figure) (2) | polycarbonate flat membrane, 0.2μ, 0.8 m² | ion-exchange resin 100 g, nylon, 100 μ | 18 | phenobarbital 150 Kg | 100–230 ml/min 3 hr. | 39% | erythrocyte 8% platelet 10% | + |
| 4 | Figure 1 (Figure) (3) | cellulose acetate hollow fiber, 0.5 μ, 0.5 m² | active carbon 150 g, inlet nylon 100 μ, outlet polyester 150 μ, cellulose acetate 5 μ, 0.5 μ | 16 | phenobarbital 150 mg/Kg | 150–200 ml/min 3 hr. | 15% | erythrocyte 0% platelet 1% | +++ |

As shown in the above-mentioned specific Examples, when the system of the present invention is used in removing useless substances from blood to purify the latter, blood can be purified with a high efficiency, without damaging and reducing blood cells and also without any fear of embolism due to the flowing-out of fine powder from the purifying agent.

What is claimed is:

1. A blood treating system having a path for causing blood to flow formed in series comprising a blood introducing part; an element for mixing blood with blood plasma;

a blood plasma-separating element having a porous membrane which passes blood plasma in blood but does not pass any blood corpuscle therein;

an element for mixing the resulting concentrated blood with blood plasma; and a purified blood-withdrawing portion in the system;

and also a path for causing blood plasma to flow comprising means for transporting blood plasma separated in said blood plasma-separating element comprising a pump;

means for purifying blood plasma separated in said blood plasma-separating element and having at its inlet and exit, a filter having a purifying agent for removing unnecessary substances in blood plasma, filled therein and capable of preventing the purifying agent from flowing out; and a three-way cock, said path for blood plasma to flow being formed between said blood plasma-separating element, said element for mixing blood with blood plasma, and said element for mixing the resulting concentrated blood with blood plasma and is so constructed that blood plasma separated in said blood plasma-separating element and purified in said means for purifying blood plasma can be sent optionally to either of said element for mixing blood with blood plasma or said element for mixing the resulting concentrated blood with blood plasma.

2. A blood treating system according to claim 1 wherein said porous membrane is hollow fiber.

3. A blood treating system according to claim 2 wherein said hollow fibers are made of cellulose acetate.

4. A blood treating system having a path for causing blood to flow formed in series comprising a blood introducing part; an element for mixing blood with blood plasma;

a blood plasma-separating element having a porous membrane which passes blood plasma in blood but does not pass any blood corpuscle therein;

and a purified blood-withdrawing portion in the system;

and also a path for causing blood plasma to flow comprising means for transporting blood plasma separated in said blood plasma-separating element comprising a pump; and means for purifying blood plasma separated in said blood plasma-separating element and having at its inlet and exit a filter having a purifying agent for removing unnecessary substances in blood plasma, filled therein and capable of preventing the purifying agent from flowing out, said path for blood plasma to flow being formed between said blood plasma-separating element and said element for mixing blood with blood plasma, and is so constructed that blood plasma separated in said blood plasma-separating element and purified in said means for purifying blood plasma can be again mixed with blood prior to the separation of blood plasma in said element for mixing blood with blood plasma.

5. A blood treating system according to one of claims 1 or 4 wherein said blood plasma-separating element contains porous artificial membrane having a size of 1μ–80 A.

6. A blood treating system according to one of claims 1 or 4 wherein said means for purifying is filled with active carbon.

7. A blood treating system according to one of claims 1 or 4 wherein said means for purifying is provided with porous filter having a pore size of 1,000μ–0.05μ.

* * * * *